(12) United States Patent
Cropper et al.

(10) Patent No.: US 8,262,675 B2
(45) Date of Patent: Sep. 11, 2012

(54) METHODS AND DEVICES FOR APPLYING MULTIPLE SUTURE ANCHORS

(75) Inventors: Michael S. Cropper, Edgewood, KY (US); David Martin, Milford, OH (US); Jonathan A. Coe, Denver, CO (US); Richard F. Schwemberger, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 806 days.

(21) Appl. No.: 12/260,414

(22) Filed: Oct. 29, 2008

(65) Prior Publication Data

US 2010/0106166 A1 Apr. 29, 2010

(51) Int. Cl.
*A61B 17/10* (2006.01)

(52) U.S. Cl. ........ 606/139; 606/142; 606/144; 606/148; 606/232

(58) Field of Classification Search .................. 606/139, 606/142–148, 232, 300, 151, 157–158, 213, 606/215–216, 222–224; 623/13.13–13.14; 289/17

See application file for complete search history.

(56) References Cited

U.S. PATENT DOCUMENTS

| | | | | |
|---|---|---|---|---|
| 5,100,415 A | * | 3/1992 | Hayhurst | 606/139 |
| 5,268,001 A | | 12/1993 | Nicholson et al. | |
| 5,391,182 A | * | 2/1995 | Chin | 606/213 |
| 5,507,757 A | * | 4/1996 | Sauer et al. | 606/144 |
| 5,573,540 A | | 11/1996 | Yoon | |
| 5,810,845 A | * | 9/1998 | Yoon | 606/139 |
| 6,117,144 A | * | 9/2000 | Nobles et al. | 606/144 |
| 6,290,674 B1 | * | 9/2001 | Roue et al. | 604/107 |
| 6,315,784 B1 | | 11/2001 | Djurovic | |
| 6,447,524 B1 | | 9/2002 | Knodel et al. | |
| 6,524,316 B1 | | 2/2003 | Nicholson et al. | |
| 6,626,930 B1 | * | 9/2003 | Allen et al. | 606/213 |
| 6,699,263 B2 | | 3/2004 | Cope | |
| 6,896,685 B1 | | 5/2005 | Davenport | |
| 6,911,034 B2 | * | 6/2005 | Nobles et al. | 606/144 |

(Continued)

FOREIGN PATENT DOCUMENTS

EP 1808134 A2 7/2007

(Continued)

OTHER PUBLICATIONS

Internation Search Report, Application PCT/US2009/057408, mailed Dec. 16, 2009, 9 pages.

(Continued)

*Primary Examiner* — Corrine M McDermott
*Assistant Examiner* — Mark Mashack
(74) *Attorney, Agent, or Firm* — Nutter McClennen & Fish LLP

(57) ABSTRACT

Methods and devices are provided for deploying and applying multiple suture anchors. In one embodiment, a surgical device is provided having a shaft configured to be introduced into a body, e.g., through a scoping device, and to deliver a plurality of suture anchors, each having a suture attached thereto, into tissue, preferably without the need to remove the shaft from the body. The shaft can be configured to penetrate tissue and to deploy one or more of the suture anchors through the tissue such that the sutures extending from the deployed suture anchors extend through the tissue to allow the anchors to engage the tissue. The surgical device can also include a knotting mechanism configured to secure the sutures attached to the deployed anchors, thereby securing the anchors to the tissue.

14 Claims, 11 Drawing Sheets

U.S. PATENT DOCUMENTS

| | | |
|---|---|---|
| 7,722,629 B2 * 5/2010 | Chambers | 606/144 |
| 7,744,613 B2 * 6/2010 | Ewers et al. | 606/153 |
| 7,824,382 B2 * 11/2010 | Reihl et al. | 604/272 |
| 7,887,551 B2 * 2/2011 | Bojarski et al. | 606/139 |
| 2002/0049453 A1 * 4/2002 | Nobles et al. | 606/139 |
| 2003/0009177 A1 1/2003 | Middleman et al. | |
| 2003/0195562 A1 10/2003 | Collier et al. | |
| 2003/0204195 A1 10/2003 | Keane et al. | |
| 2004/0162568 A1 8/2004 | Saadat et al. | |
| 2004/0186486 A1 9/2004 | Roue et al. | |
| 2004/0230095 A1 11/2004 | Stefanchik et al. | |
| 2005/0113851 A1 * 5/2005 | Swain et al. | 606/151 |
| 2005/0267533 A1 12/2005 | Gertner | |
| 2006/0025819 A1 2/2006 | Nobis et al. | |
| 2006/0030885 A1 2/2006 | Hyde | |
| 2006/0142784 A1 6/2006 | Kontos | |
| 2007/0005080 A1 1/2007 | Wolniewicz et al. | |
| 2007/0032823 A1 2/2007 | Tegg | |
| 2007/0073342 A1 3/2007 | Stone et al. | |
| 2007/0100348 A1 5/2007 | Cauthen et al. | |
| 2007/0100354 A1 5/2007 | Cauthen, III et al. | |
| 2007/0112384 A1 5/2007 | Conlon et al. | |
| 2007/0112385 A1 5/2007 | Conlon | |
| 2007/0260273 A1 11/2007 | Cropper et al. | |
| 2007/0270889 A1 11/2007 | Conlon et al. | |
| 2008/0086172 A1 4/2008 | Martin et al. | |
| 2008/0097483 A1 4/2008 | Ortiz et al. | |
| 2008/0103527 A1 5/2008 | Martin et al. | |
| 2008/0161850 A1 7/2008 | Weisenburgh et al. | |
| 2008/0275474 A1 11/2008 | Martin et al. | |
| 2010/0076462 A1 3/2010 | Bakos et al. | |
| 2010/0076488 A1 3/2010 | Spivey et al. | |

FOREIGN PATENT DOCUMENTS

| | | |
|---|---|---|
| EP | 1938760 A1 | 7/2008 |
| FR | 2785171 A1 | 5/2000 |
| WO | WO-0222026 A1 | 3/2002 |
| WO | WO-2008137534 | 11/2008 |
| WO | WO-2008137537 | 11/2008 |

OTHER PUBLICATIONS

International Search Report, Application No. PCT/US2009/057415, mailed Jan. 28, 2010, 8 pages.

International Search Report, Application No. PCT/US2009/061616, mailed Mar. 5, 2010, 8 pages.

Written Opinion for PCT/US2009/057408 dated Dec. 16, 2009 (7 pages).

Written Opinion for PCT/US2009/057415 dated Jan. 28, 2010 (7 pages).

Written Opinion for PCT/US2009/061616 dated Mar. 5, 2010 (7 pages).

* cited by examiner

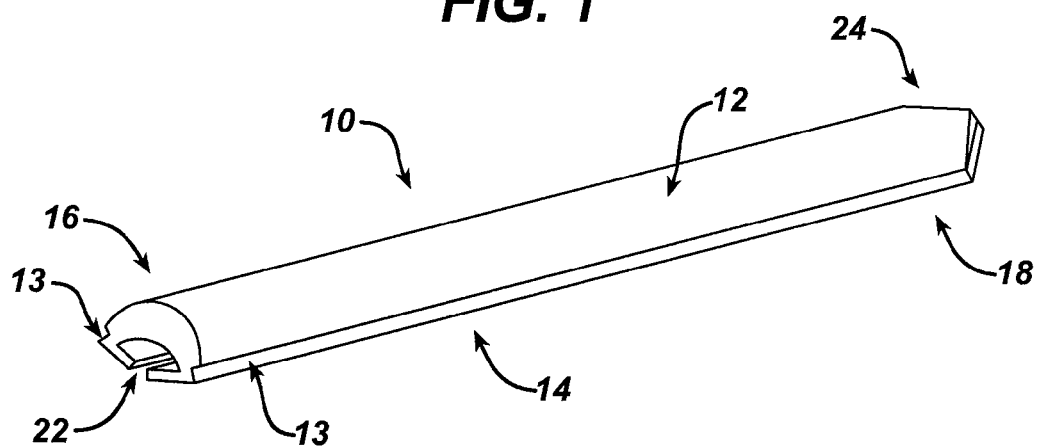
FIG. 1
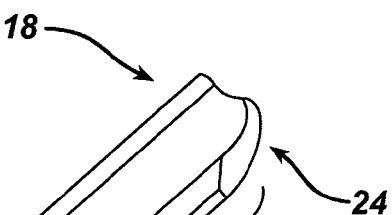
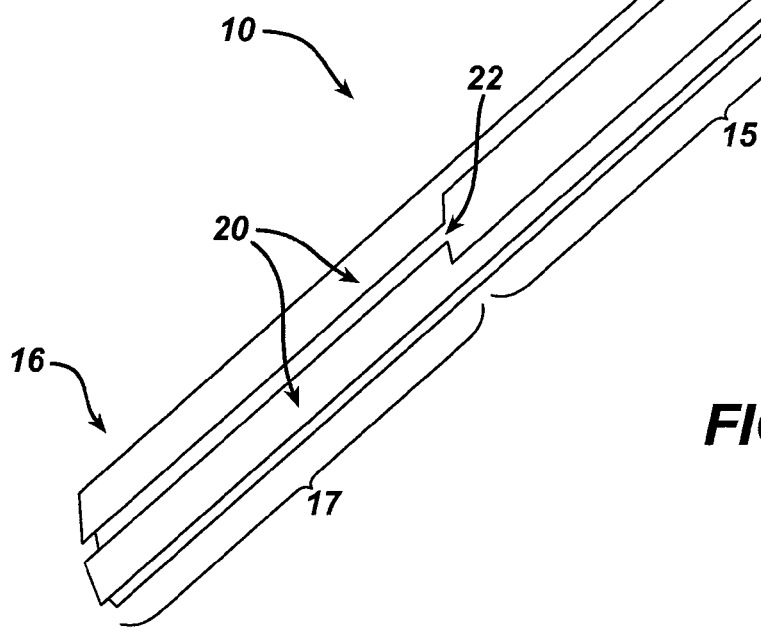
FIG. 2

METHODS AND DEVICES FOR APPLYING MULTIPLE SUTURE ANCHORS

FIELD OF THE INVENTION

The present invention relates to suture anchors and associated devices and methods for endoscopically suturing tissue.

BACKGROUND OF THE INVENTION

Endoscopic surgery, including procedures performed by way of endoscopic instruments such as gastroscopes, colonoscopes, laparoscopes, and the like, may be preferred as an alternative to open surgery due to the many advantages attributed to such "minimally invasive" techniques, such as shortened hospital stays, reduced recovery time, reduced risk of complications, and diminishment of the amount of and/or visibility of scarring caused by a surgical intervention. In many endoscopic procedures, as in open surgery, there are instances where a surgeon may desire to repair damaged or diseased tissues by apposing the tissues together using a suture. However, the suturing devices, stapling devices, and other fastener applicators that have been developed to aid surgeons performing open surgery generally cannot be easily redesigned to be passed through a flexible endoscopic instrument, which may have a working channel having an internal diameter in the range of about 2.0 to 4.0 millimeters (mm). In addition, surgeons performing endoscopic procedures generally cannot simultaneously manipulate multiple devices fed through such working channels with sufficient ease to permit them to routinely emulate the "pass and catch" suturing techniques that may be employed in open surgery.

To address these problems, various suture anchors and applicator devices have been developed to permit surgeons to endoscopically emplace sutures within tissues. Such suture anchors may be deployed using applicator devices that are inserted within and extended through the working channel of an endoscope, carrying a suture anchor to the site of repair. The applicators typically include a cannulated needle portion which permits the surgeon to penetrate the tissues adjacent to diseased or damaged tissue and to deploy the suture anchor into the tissue to be apposed in a repair. The suture anchor is generally attached to a distal end of a suture, with the bulk of the suture extending alongside or within a portion of the applicator device and with a proximal end of the suture trailing outside the endoscopic instrument. The surgeon may deploy multiple suture anchors around the site of repair by serially passing multiple applicators through a flexible endoscope to the site of repair, or by repeatedly passing and withdrawing a single applicator that may be serially reloaded with additional suture anchors. After deploying the suture anchors, the surgeon may appose the tissue by applying traction to the proximal ends of the sutures and securing the sutures using at least one additional surgical device such as a grasper or a knot pusher device. The repeated insertion of each suture anchor and/or the repeated insertion, operation, and withdrawal of one or more endoscopic devices can increase the complexity of the endoscopic procedure as well as the complexity of equipment inventory and management within the operating environment.

Accordingly, there remains a need for methods and devices for deploying and securing multiple suture anchors.

SUMMARY OF THE INVENTION

The present invention generally provides methods and devices for deploying and applying multiple suture anchors. In one embodiment, a surgical device is provided that includes an elongate shaft having a distal tissue-penetrating tip, a plurality of suture anchors releasably coupled to the shaft and configured to have the tissue-penetrating tip selectively disposed therebetween, and at least one anchor actuator, each anchor actuator configured to selectively and independently deploy the plurality of suture anchors. Each of the plurality of suture anchors has a length of suture extending therefrom.

The device can have any number of variations. For example, the device can also include a knotting mechanism disposed around the shaft and configured to apply a knotting element to the lengths of suture extending from each of the plurality of suture anchors after the plurality of anchors have been deployed. For another example, at least one of the tissue-penetrating tip and at least one of the plurality of suture anchors can be movable to selectively position the tissue-penetrating tip distally to distal ends of the plurality of suture anchors. For yet another example, the shaft can have at least one protrusion laterally extending therefrom adjacent to the tissue-penetrating tip that is configured to rotate at least one of the plurality of suture anchors when the at least one of the plurality of suture anchors is deployed. For still another example, the device can include a sheath disposed around the shaft. For another example, the device can include a handle portion engaged with the at least one anchor actuator and configured to be manipulatable outside a body. For still another example, the shaft can be flexible such that the shaft can be passed through a tortuous pathway. For yet another example, the tissue-penetrating tip of the shaft can be substantially planar and/or each of the plurality of suture anchors can have a tapered distal tip.

In some embodiments, the anchor actuator can include first and second elongate pusher shafts, the first pusher shaft being configured to deploy a first one of the plurality of suture anchors and the second pusher shaft being configured to deploy a second one of the plurality of suture anchors. A distal end of the first pusher shaft can be configured to engage a proximal end of the first one of the plurality of suture anchors, and a distal end of the second pusher shaft can be configured to engage a proximal end of the second one of the plurality of suture anchors.

In another embodiment, a surgical device includes an elongate shaft having a tissue-penetrating tip at a distal end thereof. At least two suture anchors are removably coupled to an outside surface of the shaft, each suture anchor having a suture mated thereto. The device also includes a knotting mechanism disposed around the shaft and configured to selectively apply a knotting element to the sutures mated to the at least two suture anchors. The device can have any number of variations. For example, the device can include an anchor actuator configured to selectively and independently deploy the at least two suture anchors. For another example, longitudinal axes of each of the at least two suture anchors can be substantially parallel to a longitudinal axis of the shaft at least when the at least two suture anchors are coupled to the outside surface of the shaft. For yet another example, the shaft can be configured to be disposed in a body through a working channel of a scoping device. For still another example, the sheath can be configured to have the knotting mechanism and the at least two suture anchors movably disposed therein. For yet another example, the device can include an elongate sheath, and the shaft can be movably disposed in the sheath such that the tissue-penetrating tip can selectively extend beyond a distal end of the sheath.

In other aspects, a surgical method is provided that includes disposing a surgical device into a body. The surgical device includes an elongate shaft having a tissue-penetrating tip, a plurality of suture anchors releasably coupled to the shaft and configured to have the tissue-penetrating tip selectively disposed therebetween, and at least one anchor actuator. Each of the plurality of suture anchors has a length of suture extending therefrom, and each anchor actuator is configured to selectively and independently deploy the plurality of suture anchors. The method also includes penetrating a tissue surface using the tissue-penetrating tip, and deploying at least two of the plurality of suture anchors from the shaft such that the at least two suture anchors are deployed distally to the tissue surface and the lengths of suture extending from the at least two suture anchors extend through the tissue surface. The method can have any number of variations. For example, the method can also include manipulating the surgical device to cause the tissue-penetrating tip to extend beyond distal ends of the plurality of suture anchors. For another example, the method can include securing the at least two suture anchors to tissue using a knotting mechanism disposed around the shaft and configured to apply a knotting element to the lengths of suture extending from the at least two suture anchors. For still another example, the at least two suture anchors can be sequentially deployed.

BRIEF DESCRIPTION OF THE DRAWINGS

The invention will be more fully understood from the following detailed description taken in conjunction with the accompanying drawings, in which:

FIG. 1 is a perspective top view of one embodiment of a suture anchor;

FIG. 2 is a perspective bottom view of the suture anchor of FIG. 1;

DETAILED DESCRIPTION OF THE INVENTION

Figure 3:
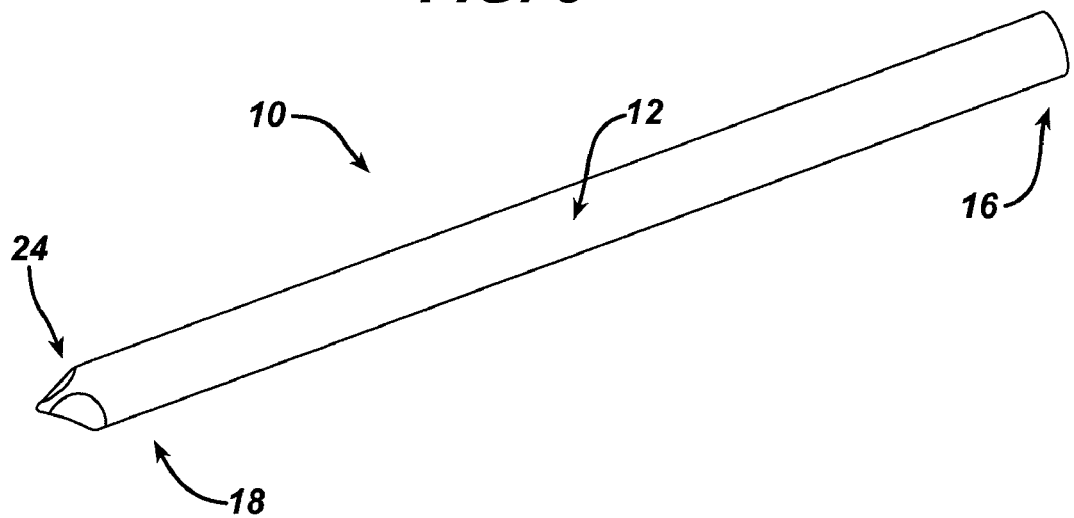
FIG. 3 is another perspective top view of the suture anchor of FIG. 1.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary methods and devices are provided for deploying and applying multiple suture anchors. In one embodiment, a surgical device is provided having a shaft configured to be introduced into a body, e.g., through a scoping device, and to deliver a plurality of suture anchors, each having a suture attached thereto, into tissue, preferably without the need to remove the shaft from the body. The shaft can be configured to penetrate tissue and to deploy one or more of the suture anchors through the tissue such that the sutures extending from the deployed suture anchors extend through the tissue to allow the anchors to engage the tissue. The surgical device can also include a knotting mechanism configured to secure the sutures attached to the deployed anchors, thereby securing the anchors to the tissue. Thus, tissue can be penetrated and multiple anchors can be deployed and secured using a single surgical device.

A person skilled in the art will appreciate that the term "tissue" as used herein is intended to encompass a variety of materials, e.g., organs, blood vessels, body lumens, and any other material that needs to be secured in a surgical procedure. A person skilled in the art will also appreciate that while the methods and devices are described in connection with endoscopic procedures in which the suture anchors are delivered through a natural orifice, the methods and devices disclosed herein can be used in numerous surgical procedures and with numerous surgical instruments. By way of non-limiting example, the devices can be used in laparoscopic procedures, in which the device is introduced percutaneously. The methods and devices can also be used in open surgical procedures. A person skilled in the art will also appreciate that the methods and devices disclosed herein can be used with any surgical tool, such as a scoping device, having a cannula or other working channel through which the shaft of a surgical instrument can be advanced and that is configured to be inserted into a body, such as through a natural orifice, through a puncture hole formed in tissue, and in any other way appreciated by a person skilled in the art. Non-limiting examples of a scoping device include an endoscope, a laparoscope, and a colonoscope. While the scoping device can be rigid or flexible, in an exemplary embodiment, the scoping device is flexible. Furthermore, the scoping device can be configured to pass through any portion of a body, but in an exemplary embodiment, the scoping device is configured to pass through a tortuous pathway. A person skilled in the art will appreciate that the term "tortuous pathway" as used herein is intended to include a tubular body lumen or organ, e.g., the colon or esophagus. Devices disclosed herein can alternatively or additionally be introduced into a body through an auxiliary passageway along the outside of a scoping device. One non-limiting example of a surgical instrument that provides such an auxiliary passageway can be found in U.S. Patent Publication No. 2004/0230095 filed May 16, 2003 and titled "Medical Apparatus For Use With An Endoscope," which is hereby incorporated by reference in its entirety.

The devices discussed herein can be made from any combination of rigid and/or flexible materials, but in an exemplary embodiment the materials are biocompatible. A person skilled in the art will appreciate that the term "flexible" as used herein is intended to encompass a variety of configurations. Generally, a "flexible" member has some degree of elasticity, e.g., is capable of bending without breaking. In an exemplary embodiment, the device or at least portions thereof are composed of at least one biocompatible and flexible material, e.g., plastic, titanium, stainless steel, etc. Various portions of the device can also be formed from a shape memory material, such as Nitinol.

The suture anchors coupled to and deployable from the shaft can include any suture anchor having a suture attached thereto in any way appreciated by a person skilled in the art. The suture anchor can be configured to secure tissue with its attached suture, as will also be appreciated by a person skilled in the art. Each suture anchor coupled to the shaft can be the same or different from any one or more other suture anchors coupled to the shaft, but in an exemplary embodiment, each suture anchor coupled to the shaft is identical. Any size and shape of suture anchor can be used with the device. The suture anchor can be composed of any one or more materials as will be appreciated by a person skilled in the art, e.g., titanium, tantalum, stainless steel, a shape memory material, plastic, etc. In an exemplary embodiment, the suture anchor is composed of a rigid material such as stainless steel or titanium. The suture anchor can also have a fixed configuration, or expandable suture anchors can be used. For example, the suture anchor can be constrainable to a first configuration for deployment into tissue (e.g., when coupled to the shaft) and be expandable when unconstrained to a second configuration (e.g., when deployed from the shaft) for resisting pull-out from the tissue, such as when the suture anchor is composed of a shape memory material.

FIGS. 1-3 illustrate one exemplary embodiment of a suture anchor 10 that can be delivered and applied using the methods and devices described herein. The anchor 10 can have any shape, size, and configuration. The anchor 10 can have a uniform or non-uniform diameter along its longitudinal length and preferably has a diameter that allows the anchor 10 to be coupled to a shaft and/or disposed within a sheath as discussed further below.

The illustrated anchor 10 generally includes an elongate body that is configured to be positioned along a tissue surface and that includes a suture coupled thereto, preferably to a mid-portion thereof. Such a configuration allows the elongate body to be inserted through tissue along the elongate body's longitudinal axis and then to pivot, e.g., about 90 degrees, to rest against and engage the tissue surface. The suture attached to the elongate body will extend through the tissue, thus allowing the suture to be used to reposition, tension, secure, or otherwise manipulate the tissue. While the elongate body can have various configurations, in an exemplary embodiment, the elongate body includes at least a portion that is configured to seat the suture to facilitate insertion of the suture anchor through tissue.

In the illustrated embodiment, the elongate body has outer and inner sides 12, 14 and proximal and distal ends 16, 18. In some embodiments, any portion of one or both of the outer and inner sides 12, 14 can be substantially planar, or as illustrated, the outer and inner sides 12, 14 can be curved. Indented side tracks 13 can extend along at least a portion of the anchor's longitudinal length between the outer and inner sides 12, 14 on opposed sides of the anchor 10. The body can have a partially cylindrical shape where the outer side 12 can be substantially convex to help the anchor 10 more easily pass through tissue and/or a surgical device. The inner side 14 can be substantially concave with a hollow interior and can be configured to seat a suture to the anchor 10. The inner side 14 can have a first half, referred to herein as a cannulated portion 15, and a second half, referred to herein as a bifurcated portion 17. The cannulated portion 15 can extend along any partial length of the body and can, as illustrated, be substantially smooth. The bifurcated portion 17 can also extend along any partial length of the body, although the cannulated and bifurcated portions 15, 17 preferably each have substantially the same length to allow a suture attached to the anchor 10 to extend from the anchor 10 at substantially a mid-portion thereof, e.g., at a junction of the cannulated and bifurcated portions 15, 17. Such a configuration can allow the anchor 10 to be deployed longitudinally through tissue and to pivot to engage the tissue. The suture can be any conventional surgical suture, as will be appreciated by a person skilled in the art. The suture can be composed of any material, e.g., cat gut, silk, polypropylene, polyester, stainless steel, etc., and the suture can have any shape and size, e.g., 2/0 suture, 3/0 suture, 4/0 suture, etc.

The bifurcated portion 17 can include a pair of opposed legs 20 configured to engage a suture and attach it to the anchor 10. A person skilled in the art will appreciate that the anchor 10 can be hollowed during manufacturing simply to facilitate formation of the legs 20 in the bifurcated portion 17. In other embodiments, any portion of one or both of the cannulated and bifurcated portions 15, 17 can be a solid member, e.g., without a hollowed interior extending fully or partially therethrough. The legs 20 can have any size, shape, and configuration. As illustrated, the legs 20 include two substantially planar rectangular flanges. The legs 20 can be substantially smooth and can extend substantially transverse to the longitudinal axis of the anchor 10, which can help the anchor 10 more easily slidably engage a surgical device shaft and/or contact more of a tissue surface following deployment of the anchor 10. The legs 20 can be configured to crimp a suture in a channel 22 therebetween to attach the suture to the anchor 10, although a suture can be seated to the anchor 10 in any way, as will be appreciated by a person skilled in the art. By way of non-limiting example, the suture can be crimped in a surface of the suture anchor 10, molded to the suture anchor 10, or knotted to the suture anchor 10. Non-limiting examples of various ways to attach a suture to a suture anchor are described in U.S. Patent Publication No. 2007/0112384 filed Nov. 15, 2005 and titled "Suture Anchor Applicator" and in U.S. Patent Publication No. 2008/0161850 filed Dec. 28, 2006 and titled "Suture Anchoring System," which are hereby incorporated by reference in their entireties.

The anchor's distal end 18 can include a tissue-penetrating tip 24 configured to penetrate tissue. As will be appreciated by a person skilled in the art, the penetrating tip 24 can have any size, shape, and configuration and can have any length along the longitudinal length of the anchor 10. As illustrated in this embodiment, the penetrating tip 24 can be tapered in a distal direction and angled toward a central longitudinal axis of the anchor 10, although the penetrating tip 24 can be tapered, angled, or neither. A tapered and/or angled distal end can help the anchor 10 more easily pass through tissue by reducing a force necessary to insert the anchor 10 through tissue and/or by expanding a tissue incision through which the anchor 10 is being passed.

Various other, non-limiting embodiments of suture anchors are described in previously mentioned U.S. Patent Publication Nos. 2007/0112384 and 2008/0161850 and in U.S. Patent Publication No. 2007/0112385 filed Nov. 15, 2005 and titled "Expandable Suture Anchor" and U.S. Pat. No. 6,447, 524 issued Sep. 10, 2002 and titled "Fastener For Hernia Mesh Fixation," which are hereby incorporated by reference in their entireties.

Figure 4:
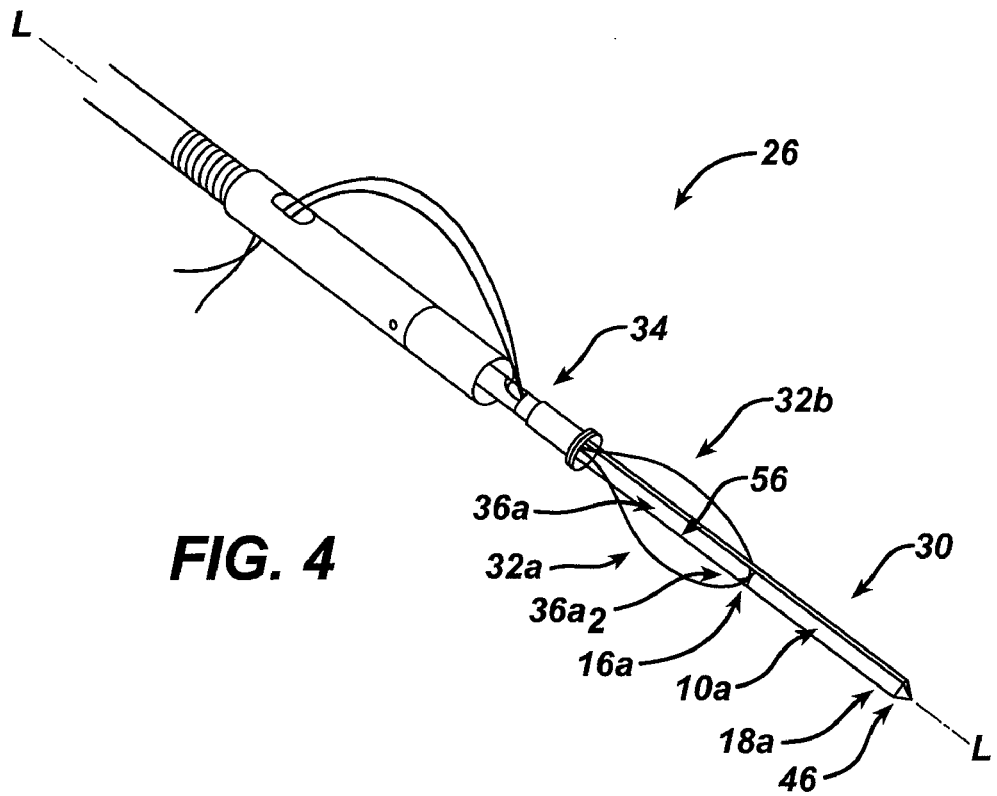
FIG. 4 is a perspective view of a distal portion of one embodiment of a surgical device configured to deliver and apply a plurality of suture anchors.
Figure 5:
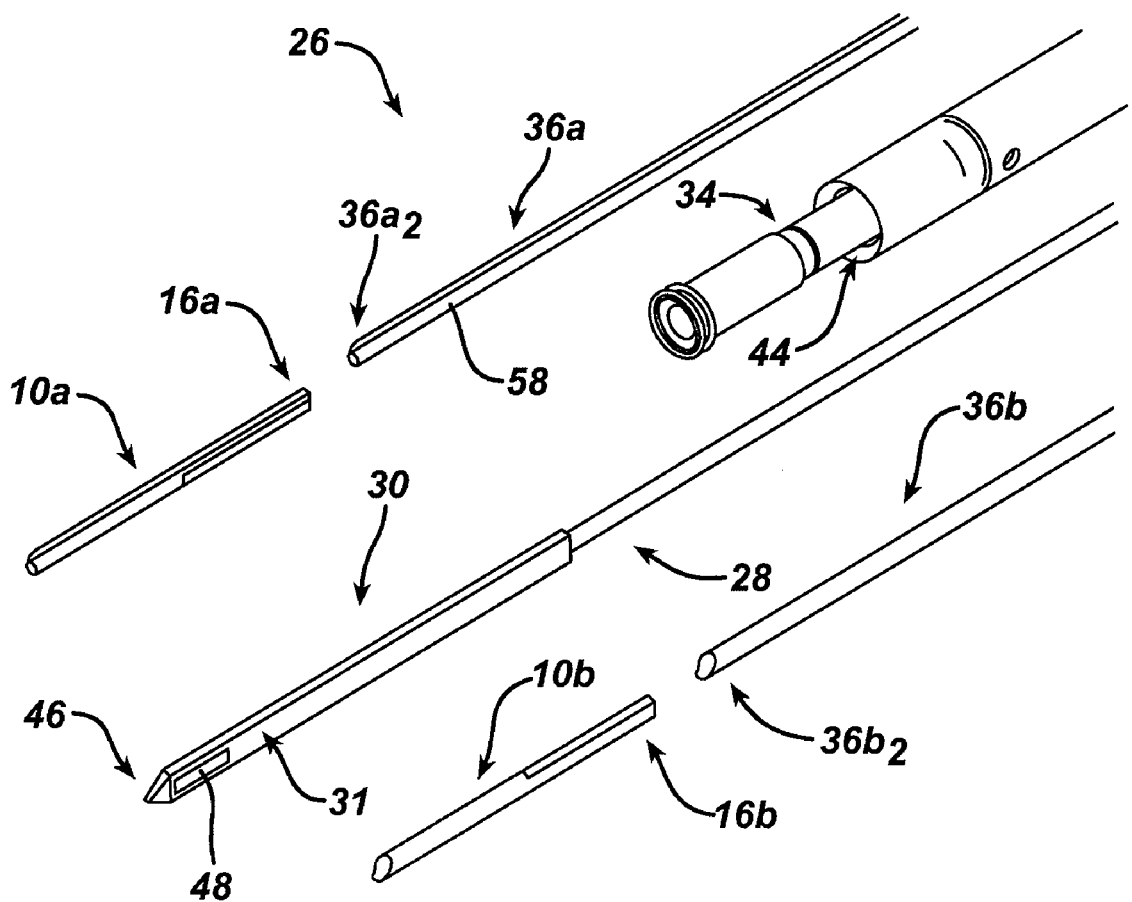
FIG. 5 is an exploded view of the distal portion of the device of FIG. 4.
Figure 6:
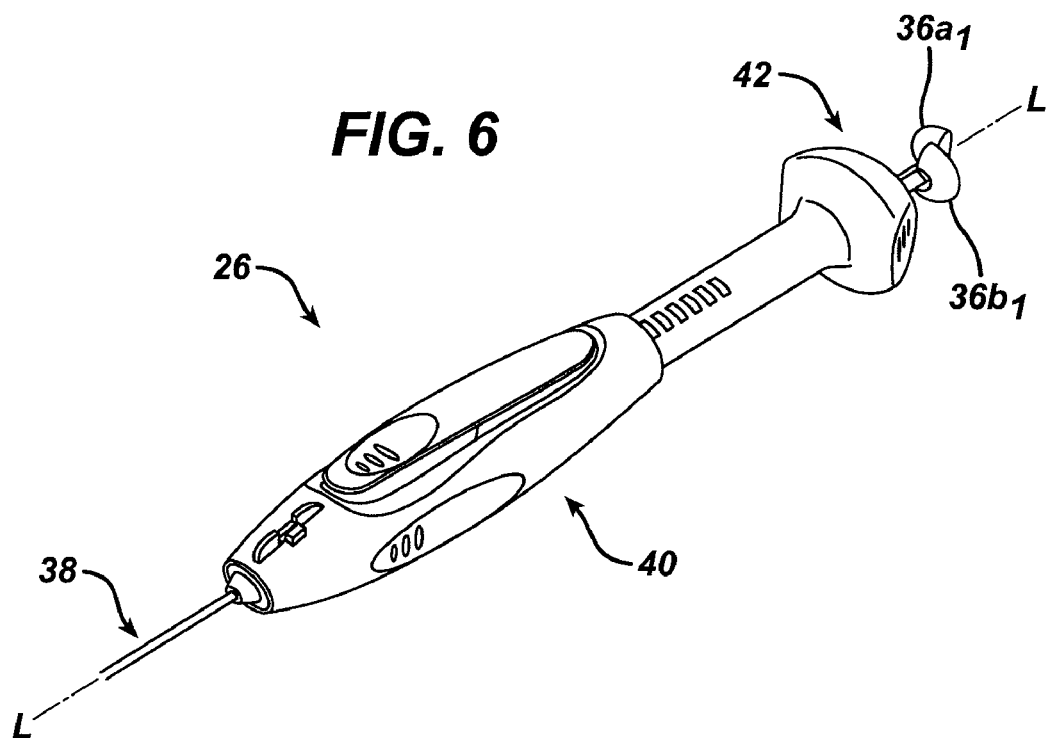
FIG. 6 is a perspective view of a proximal portion of the device of FIG. 4.

FIG. 4-6 illustrate a surgical device 26 configured to deliver and apply at least one of a plurality of suture anchors to tissue at a surgical site in a body of a patient. In an exemplary embodiment, the device 26 has an elongate shaft 28 that can be flexible to allow it to be introduced into a body of a patient usually in a minimally invasive technique, such as through a working channel of a flexible scoping device (or through an auxiliary channel of a flexible scoping device) having at least its distal end disposed in a body. A person skilled in the art will appreciate that having a flexible shaft indicates that at least a portion of the shaft 28 is composed of one or more flexible materials. The shaft 28 can be configured to have the plurality of anchors, e.g., first and second suture anchors 10a, 10b each similar to the anchor 10 shown in FIGS. 1-3, having respective first and second sutures 32a, 32b attached thereto removably coupled at a distal portion 30 of the shaft 28. The device 26 is illustrated with two suture anchors 10a, 10b coupled to an outside surface of the shaft 28, but the shaft 28 can have any number of suture anchors coupled thereto. Longitudinal axes of each of the anchors 10a, 10b can be substantially parallel to a longitudinal axis of the shaft 28 at least when the anchors 10a, 10b are coupled to the outside surface of the shaft 28, as illustrated in FIG. 4. The shaft 28 can also be slidably engaged with at least one anchor actuator configured to selectively and independently deploy the anchors 10a, 10b. The anchor actuator can have a variety of configurations, but as illustrated in this exemplary embodiment, the anchor actuator includes first and second elongate pusher shafts 36a, 36b configured to respectively deploy the first and second anchors 10a, 10b. The shaft 28 can also be configured to be movably disposed through a knotting mechanism 34 that is configured to engage the sutures 32a, 32b attached to the anchors 10a, 10b and to knot the sutures 32a, 32b following deployment of the anchors 10a, 10b. The device 26 can also include an outer tube or cannulated sheath 38 in which the anchors 10a, 10b, the shaft 28, the knotting mechanism 34, and the anchor actuator can be selectively and movably disposed.

The sheath 38 at its proximal end can be coupled to a handle portion 40 of the device 26. As will be appreciated by a person skilled in the art, the handle portion 40 can have any size, shape, and configuration to allow manipulation of the device 26 outside the body to deploy the anchors 10a, 10b therefrom and to knot their attached sutures 32a, 32b using the knotting mechanism 34. Various non-limiting embodiments of handles are described in previously mentioned U.S. Patent Publication No. 2007/0112384 and in U.S. Patent Publication No. 2008/0103527 filed Oct. 27, 2006 and titled "Flexible Endoscopic Suture Anchor Applier," which is hereby incorporated by reference in its entirety. Any portion of the sheath 38, the shaft 28, the knotting mechanism 34, and/or the anchor actuator can extend through the handle portion 40 and out a proximal end 42 of the handle portion 40 to help actuate various aspects of the device 26. For example, as illustrated, the pusher shafts 36a, 36b can be slidably engaged with the handle portion 40 and have proximal, handle ends $36a_1$, $36a_2$ that extend out the proximal end 42 of the handle portion 40 such that the pusher shafts 36a, 36b can be selectively and independently moved using the handle ends $36a_1$, $36a_2$.

As discussed further below, each of the plurality of suture anchors 10a, 10b coupled to the shaft 28 can be deployed from the shaft 28 sequentially and/or simultaneously with any number of the other anchors 10a, 10b. In an exemplary embodiment, the first and second anchors 10a, 10b can be configured to engage the anchor actuator, e.g., proximal ends 16a, 16b of the anchors 10a, 10b can be configured to respectively engage distal ends $36a_2$, $36b_2$ of the pusher shafts 36a, 36b. The proximal ends 16a, 16b of the anchors 10a, 10b can optionally include an engagement mechanism to help the anchors 10a, 10b engage their respective pusher shafts 36a, 36b, which can also include a corresponding engagement mechanism. Alternatively or in addition, the proximal ends 16a, 16b of the anchors 10a, 10b can have shapes corresponding to shapes of the distal ends of their respective pusher shafts 36a, 36b to help ensure adequate contact and transmitted motion between the anchors 10a, 10b and the pusher shafts 36a, 36b. The first anchor 10a can be deployed from the shaft 28 by advancing the first pusher shaft 36a relative to the first anchor 10a, e.g., by pushing on the proximal handle end $36a_1$ of the first pusher shaft 36a, to engage the first pusher shaft's distal end $36a_2$ with the first anchor's proximal end 16a and advance the first anchor 10a from the shaft 28. In other words, longitudinal motion of the first pusher shaft 36a can translate to the first anchor 10a, thereby deploying the first anchor 10a. The second pusher shaft 36b can be used to similarly deploy the second anchor 10b. In this way, multiple suture anchors coupled to the shaft 28 can be simultaneously introduced into a body and can be selectively and independently deployed from the shaft 28 in any number, in any order, and at any placement within the body as needed during a surgical procedure without the shaft 28 having to be removed from the body, thereby saving time and reducing chances of the shaft 28 introducing any unwanted fluid or tissue debris into the body and/or a cannula through which the shaft 28 is repeatedly introduced and removed from the body.

The shaft 28 can have a variety of sizes, shapes, and configurations. Generally, the shaft 28 can have a shape, size, and configuration that allows it to releasably engage inner sides of the first and second anchors 10a, 10b, as discussed further below, and to be movably disposed through the knotting element 34 and the sheath 38. The shaft 28 can be rigid, flexible, or a combination thereof, but it is preferably flexible at least along a substantial length thereof. Portions of the shaft's distal portion 30 can be less flexible or more rigid than the remainder of the shaft 28 to facilitate insertion through tissue and/or anchor deployment. The shaft 28 is preferably solid, but the shaft 28 can have one or more hollow portions.

The shaft 28 can have any longitudinal length, but its length is preferably long enough to allow the shaft's proximal portion to extend into and/or proximally beyond the handle portion 40 of the device 26 to allow the shaft 28 to be manipulated outside the body when the shaft's distal portion 30 is disposed in a body and/or in a scoping device.

In an exemplary embodiment, the shaft 28 can be substantially cylindrical to help the shaft 28 pass smoothly into a body, except in the distal portion 30, which can be substantially planar to help the shaft 28 penetrate tissue and couple to the anchors 10a, 10b. The shaft 28 can have any constant or varying shape along its longitudinal length, and the diameter can be uniform or non-uniform along its longitudinal length. In an exemplary embodiment, the shaft 28 has a substantially uniform diameter along its longitudinal length except in its distal portion 30, which has a larger diameter to help engage the anchors 10a, 10b. The distal portion 30 can have a variety of sizes, shapes, and configurations, but as shown in the illustrated embodiment, the distal portion 30 can be a flattened portion or a substantially planar tab. The shape and size of the distal portion 30 can generally correspond to the shape and size of inner sides 14a, 14b of the anchors 10a, 10b to allow the anchors 10a, 10b to couple to opposed anchor-contacting surfaces 31 of the shaft 28. The shaft 28 and the anchors 10a, 10b attached thereto can have any combined diameter, but their combined diameter in an exemplary embodiment is equal to or less than about 3.5 mm, which can allow the shaft 28 and the anchors 10a, 10b to be disposed through a working channel of a scoping device having a conventional diameter of about 3.7 mm.

Figure 7:
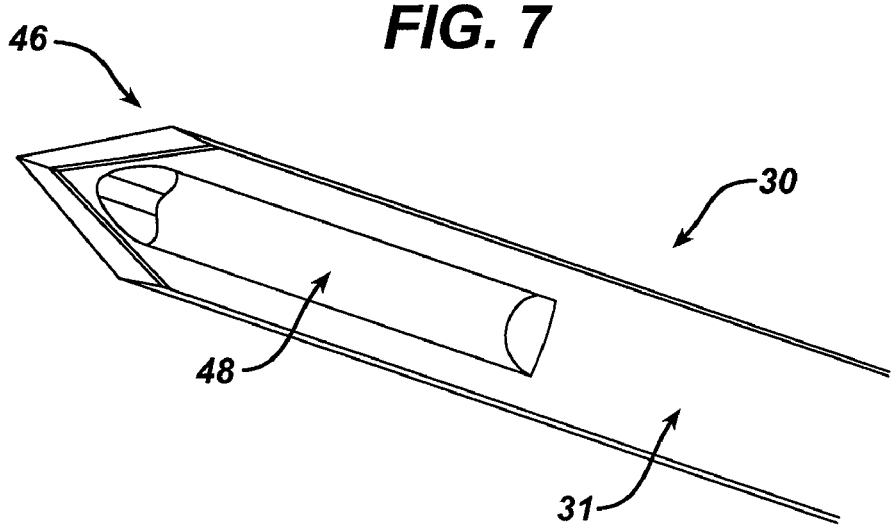
FIG. 7 is a perspective view of a shaft of the device of FIG. 4.
Figure 8:
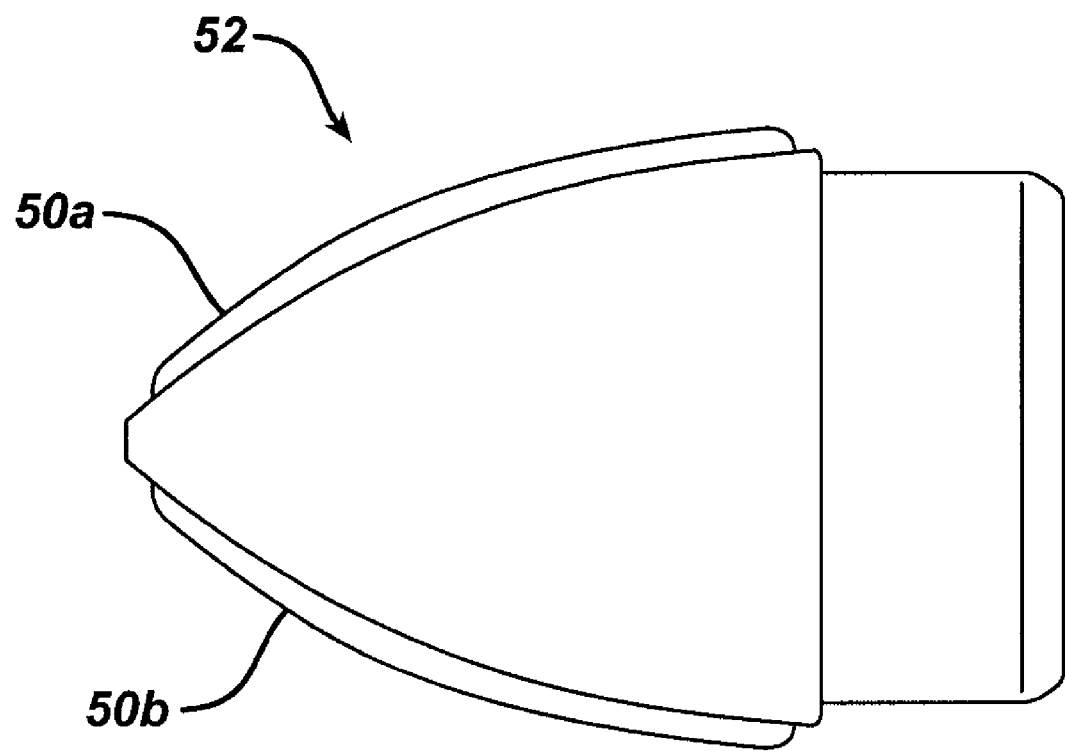
FIG. 8 is a side view of one embodiment of a tissue-penetrating tip.

The shaft 28 can be inserted through tissue in a variety of ways, as will be appreciated by a person skilled in the art. For non-limiting example, a needle, a knife, or other cutting element can be introduced to the body through a scoping device and/or in any other way appreciated by a person skilled in the art and can be used to cut tissue at a desired location. In this exemplary embodiment, as best shown in FIGS. 4 and 5 and in closer detail in FIG. 7, a tissue-penetrating tip 46 at a distal-most end of the shaft 28 can be used to penetrate tissue. The tip 46 can have a variety of shapes, sizes, and configurations. In an exemplary embodiment, the tip 46 has a longitudinal length of less than about 0.75 inches (about 1.9 centimeters). The tip 46 can be composed of any one or more flexible and/or rigid materials, although the tip 46 is preferably rigid, e.g., composed of stainless steel, titanium, etc., with at least three times the bending rigidity of a remainder of the shaft 28 to help the tip 46 penetrate tissue. The tip 46 can be integrally formed with a reminder of the shaft 28, or it and/or the shaft's distal portion 30 can be removably or fixedly attached to the shaft 28 using, e.g., an interference fit, an adhesive, ultrasonic welding, etc. The tip 46 can have a variety of shapes, e.g., triangular (as shown), rectangular, rounded, etc. Although the tip 46 is shown as a substantially triangular, tapered, planar tip, the tip 46 can have any shape. The tip 46 can include one or more features to help it to penetrate tissue, e.g., a tapered shape, a beveled edge (including a chamfered edge, as illustrated), a pointed needle, an electronic cutter, etc. In an alternate embodiment shown in FIG. 8, a tissue-penetrating tip 52 has first and second cutting blades 50a, 50b formed on opposed sides thereof and extending between proximal and distal ends of the tip 52. The cutting blades 50a, 50b protrude above an outer surface of the tip 52, and have sharp edges to cut through tissue. The cutting blades 50a, 50b can also be configured to couple to an energy source to facilitate cutting of tissue. For example, a cautery wire can be coupled to the blades. In another embodiment, the blades can be in the form of paddles that do not cut tissue, but rather merely extend outward from an outer surface of the tip to penetrate tissue. Various non-limiting embodiments of tissue-penetrating tips that can be included on the device's shaft can be found in U.S. Patent Publication No. 2007/0260273 filed May 8, 2006 and titled "Endoscopic Translumenal Surgical Systems," hereby incorporated by reference in its entirety.

Figure 9:
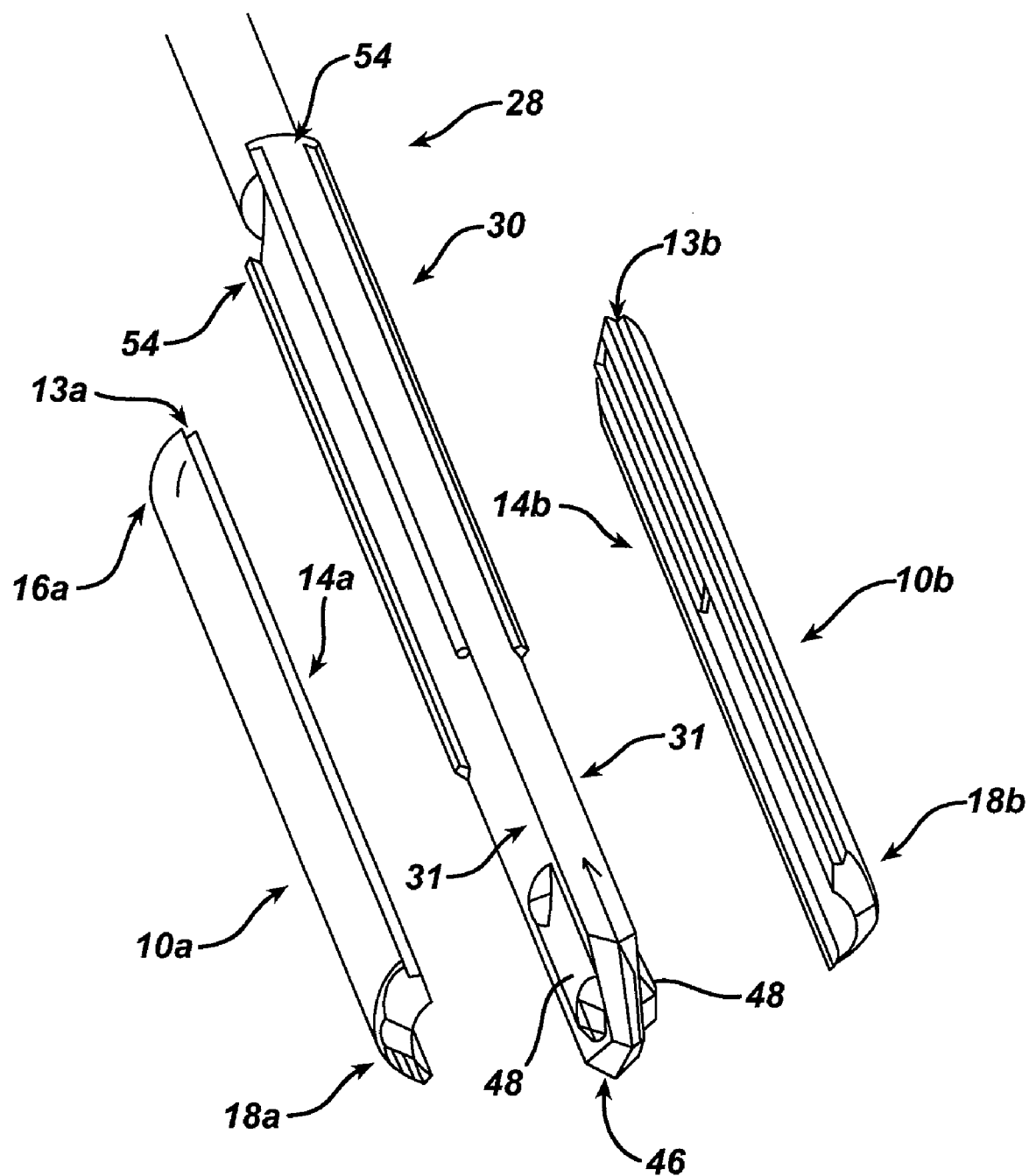
FIG. 9 is an exploded view of a shaft and a plurality of suture anchors of the device of FIG. 4.
Figure 10:
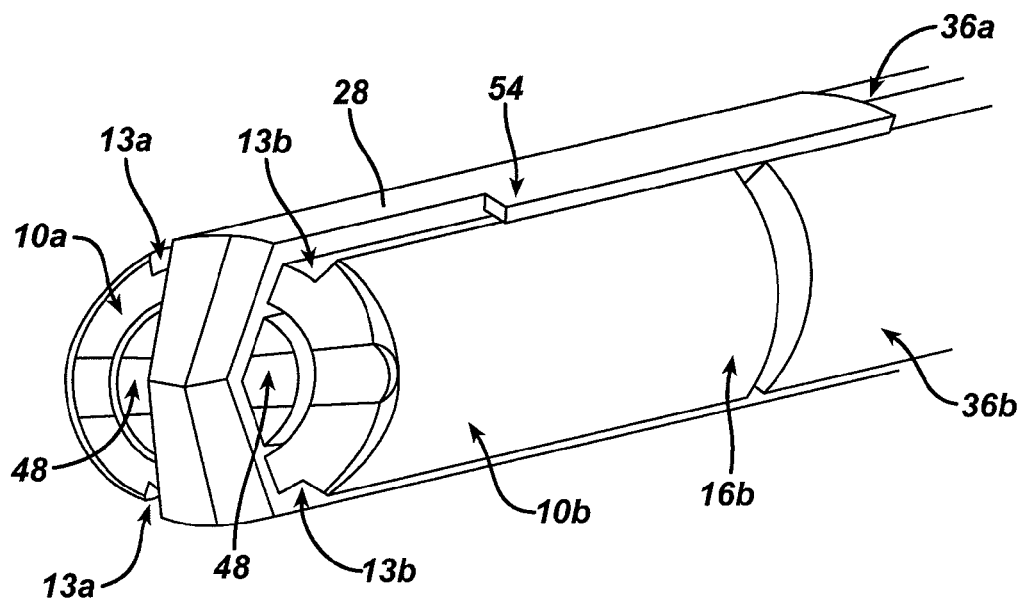
FIG. 10 is a perspective view of a shaft, a plurality of suture anchors, and an anchor actuator of the device of FIG. 4.

The shaft's distal portion 30 can include at least one flange laterally extending therefrom that is configured to engage an anchor to help fix the anchor to the shaft 28 until the anchor is deployed. The shaft 28 can have any number of flanges, and the flange(s) can have any size, shape, and configuration. In an exemplary embodiment, as illustrated in FIGS. 9 and 10, the shaft 28 can include two flanges 54 formed on opposed sides of the distal portion 30 of the shaft 28. The flanges 54 can be integrally formed with the shaft 28 or attached thereto in any way appreciated by a person skilled in the art. The flanges 54 can extend along at least a partial longitudinal length of the shaft's distal portion 30, preferably along a partial length thereof extending from a proximal end of the distal portion 30 toward the distal tip 46. The flanges 54 can have a size and shape configured to slidably engage side tracks 13a, 13b of, respectively, the first and second anchors 10a, 10b to removably couple the anchors 10a, 10b to the shaft 28. The first and second anchors 10a, 10b can be slidably loaded onto the shaft 28 by engaging at least a portion of their respective tracks 13a, 13b with their respective flanges 54 on either side of the shaft's distal portion 30, thereby coupling the first and second anchors 10a, 10b to the shaft 28 until deployed therefrom using the anchor actuator. The flanges 54 can also be configured to axially guide the anchors 10a, 10b engaged therewith to help the anchors 10a, 10b more easily and directly penetrate tissue. The first and second pusher shafts 36a, 36b can be similarly slidably loaded onto the shaft 28, e.g., with distal portions of the first and second pusher shafts 36a, 36b slid onto the flanges 54, which can help the pusher shafts 36a, 36b guide and deploy their respective anchors 10a, 10b.

The shaft's distal portion 30 can also include at least one ramp or protrusion laterally extending therefrom adjacent to the tip 46 that is configured to rotate at least one of the anchors 10a, 10b coupled to the shaft 28 when the at least one of the anchors 10a, 10b is deployed. The shaft 28 can include any number of protrusions, and the protrusion(s) can have any size, shape, and configuration. The protrusions preferably have a shape and size configured to complement the inner sides 14a, 14b of the first and second anchors 10a, 10b to help seat the anchors 10a, 10b to the shaft 28 and to help rotate the anchors 10a, 10b when they are deployed therefrom. The protrusions can be tapered in a distal direction and/or angled toward a central longitudinal axis of the shaft 28 to help the shaft 28 more easily pass through tissue. In the illustrated exemplary embodiment, as best seen in FIGS. 5, 7, 9, and 10, two protrusions 48 laterally extend from the distal portion 30, one on each of the anchor-contacting surfaces 31 on opposed sides of the distal portion 30. The protrusions 48 can thus be configured to engage the first and second anchors 10a, 10b when the first and second anchors 10a, 10b are coupled to the shaft 28, as best seen in FIG. 10. The protrusions 48 can help eject the anchors 10a, 10b with which they are respectively engaged by helping to push the anchors 10a, 10b away from the shaft 28 when the anchors 10a, 10b are disengaged from their respective flanges 54.

The shaft's distal portion 30 can also include one or more graspers (not shown) located adjacent the tip 46 and configured to grasp tissue and to provide tension to the tissue during penetration by the tip 46. The grasper(s) can be actuated in any way, e.g., using a control at the handle portion 40, as will be appreciated by a person skilled in the art. A person skilled in the art will also appreciate that the term "grasper" as used herein is intended to encompass any surgical instrument or mechanism that is configured to grab and/or attach to tissue and thereby manipulate the tissue, e.g., forceps, retractors, movable jaws, magnets, adhesives, etc.

As mentioned above, the shaft 28 can be movable, manually and/or electronically, relative to at least one other component of the device 26 and/or to a scoping device in which the shaft 28 is disposed. The shaft 28 can be movable in any one or more ways, but in an exemplary embodiment, the shaft 28 is slidably and rotatably movable relative to the sheath 38 within an inner pathway 44 of the sheath 38. The shaft 28 can be slidably movable along a central longitudinal axis L of the device 26 to allow the distal portion 30 of the shaft 28 to be selectively advanced beyond the sheath's distal end to penetrate tissue and to deploy the anchors 10a, 10b. The shaft 28 can also or instead be rotatably movable about the device's central axis L to facilitate its penetration of tissue. The shaft 28 can be moved in a variety of ways, although in an exemplary embodiment, the shaft 28 can be manipulated via the handle portion 40, as will be appreciated by a person skilled in the art. Any type of handle and/or controls having any configuration can be used. For non-limiting example, the handle portion 40 can include a knob or button to help guide the device 26 into a body, slidably and/or rotationally move the shaft 28 within and relative to the sheath 38, deploy the first and/or second anchors 10a, 10b, and/or perform any other functions as will be appreciated by a person skilled in the art. The device 26 can include a locking mechanism, e.g., a catch, a switch, etc., to lock the shaft 28 in a desired position when the shaft's distal portion 30 is advanced through tissue and/or contained within and/or extends beyond the sheath's distal end, as will be appreciated by a person skilled in the art.

In some embodiments, the tip 46 of the shaft 28 can be selectively disposed between the first and second anchors 10a, 10b such that the tip 46 can selectively extend distally beyond distal ends 18a, 18b of the first and second anchors 10a, 10b, which can help prevent the tip 46 from being undesirably exposed and unintentionally penetrating or otherwise damaging tissue or other matter. The tip 46 can be selectively disposed therebetween in a variety of ways, such as by having the tip 46 and/or the anchors 10a, 10b coupled to the shaft 28 be moveable. The tip 46 can be manually and/or mechanically moveable from the handle portion 40 such that the tip 46 can be selectively retracted into and advanced from a distal end of the sheath 38 and/or the anchors 10a, 10b. Alternatively or in addition, the first and second anchors 10a, 10b can be movable relative to the tip 46 by extending the first and second anchors 10a, 10b distally beyond the tip 46, e.g., by pushing the pusher shafts 36a, 36b. In some embodiments, the first and second anchors 10a, 10b can be spring or otherwise biased toward the tip 46 and can advance to have the tip 46 disposed therebetween once the tip 46 has penetrated tissue to allow passage of the anchors 10a, 10b therethrough.

In some embodiments, a surgical device can optionally include a protective element configured to be movable relative to the device's tissue-penetrating tip to selectively extend beyond a distal-most end of the tip to help prevent the tip from being undesirably exposed and unintentionally penetrating tissue or other matter. One embodiment of a protective element includes a plunger that can have any size, shape, and configuration. In an exemplary embodiment, the plunger can be disposed within a central lumen extending through an elongate shaft having a tissue-penetrating tip formed on a distal end thereof. The plunger can be configured to be movable between a first position where the plunger is positioned distally of the tip to prevent the tip from penetrating tissue and a second position where the plunger is proximal to the tip to allow the tip to penetrate tissue and/or other matter. The plunger can be configured to be movable from the first position to the second position when the plunger is advanced into a tissue surface. The device can also include a biasing element configured to bias the plunger to the first position. The biasing element can also have any size, shape, and configuration, but in one embodiment, the biasing element can be coupled between a distal end of a stylet that extends through the central lumen of the shaft and a proximal end of the plunger. In other embodiments, the biasing element can be integrally formed with the plunger and/or the stylet.

The pusher shafts 36a, 36b, best seen in FIGS. 4, 5, and 10, can also have a variety of sizes, shapes, and configurations. The pusher shafts 36a, 36b can be identical, as shown, or they can be different. Generally, the first and second pusher shafts 36a, 36b can have a configuration that allows them to selectively and independently engage the first and second anchors 10a, 10b, respectively, when the first and second anchors 10a, 10b are coupled to the shaft 28, and to be movably disposed through the knotting element 34 and the sheath 38. The pusher shafts 36a, 36b can be rigid, flexible, or a combination thereof, but they are preferably flexible at least along a substantial length thereof. Portions of the pusher shafts' distal portions can be less flexible or more rigid than the remainder of the pusher shafts 36a, 36b to facilitate pushing of the anchors 10a, 10b. The pusher shafts 36a, 36b are preferably solid, but they can have one or more hollow portions. The pusher shafts 36a, 36b can each have any longitudinal length, but their lengths are preferably long enough to allow the pusher shafts' proximal portions to extend into and/or proximally beyond the handle portion 40 of the device 26 to allow the pusher shafts 36a, 36b to be manipulated outside the body when the device 26 in a body and/or in a scoping device.

In an exemplary embodiment, the first pusher shaft 36a can be substantially partially cylindrical, except at its proximal end, which can include the proximal handle ends 36a$_1$, as discussed above. The substantially cylindrical portion of the first pusher shaft 36a can have, as illustrated, a convex outer surface 56 and a concave inner surface 58 to help the first pusher shaft 36a pass smoothly through the sheath 38, and/or other device or channel, and the knotting element 34 and easily slide over the shaft 28. The first pusher shaft 36a can have any constant or varying shape along its longitudinal length, and its diameter can be uniform or non-uniform along its longitudinal length. In an exemplary embodiment, the first pusher shaft 36a has a substantially uniform diameter along its longitudinal length except in its distal portion, which has a larger maximum diameter to help engage the first anchor 10a. The pusher shaft's distal portion can have a variety of sizes, shapes, and configurations, but as shown in the illustrated exemplary embodiment and as mentioned above, the distal portion can be configured to generally correspond to the shape and size of the proximal end 16a of the first anchor 10a to help the first pusher shaft 36a engage and push the first anchor 10a. The second pusher shaft 36b can be configured similar to the first pusher shaft 36a.

The knotting mechanism 34, best seen in FIGS. 4, 5, 11, and 12, can have a variety of sizes, shapes, and configurations. Various non-limiting embodiments of knotting mechanisms are described in U.S. Patent Publication No. 2007/0270889 filed May 19, 2006 and titled "Combination Knotting Element And Suture Anchor Applicator," and in PCT Patent Application No. PCT/US2008/062203 entitled "Loader for Knotting Element", which are hereby incorporated by reference in their entireties.

Figure 11:
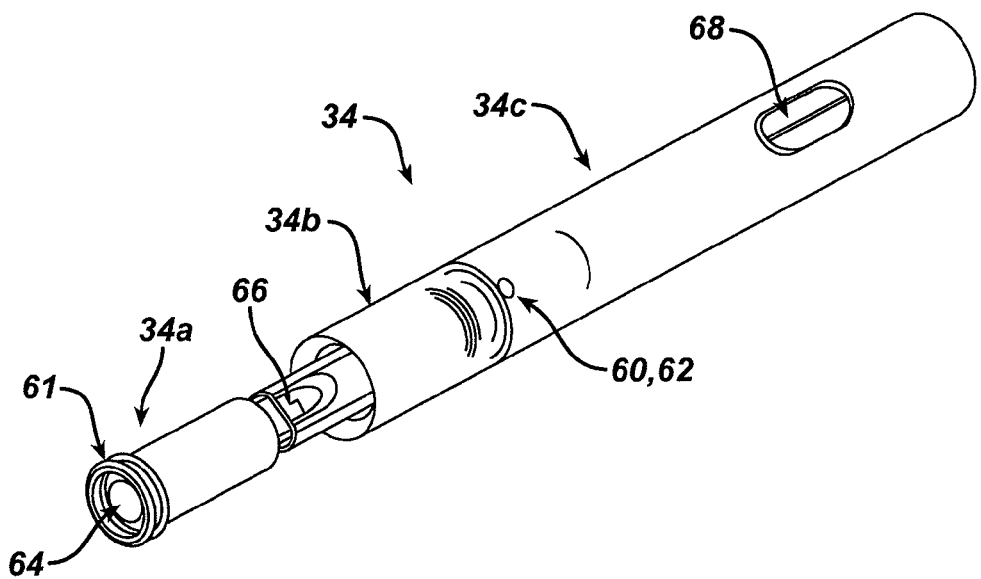
FIG. 11 is a perspective view of a knotting mechanism of the device of FIG. 4.
Figure 12:
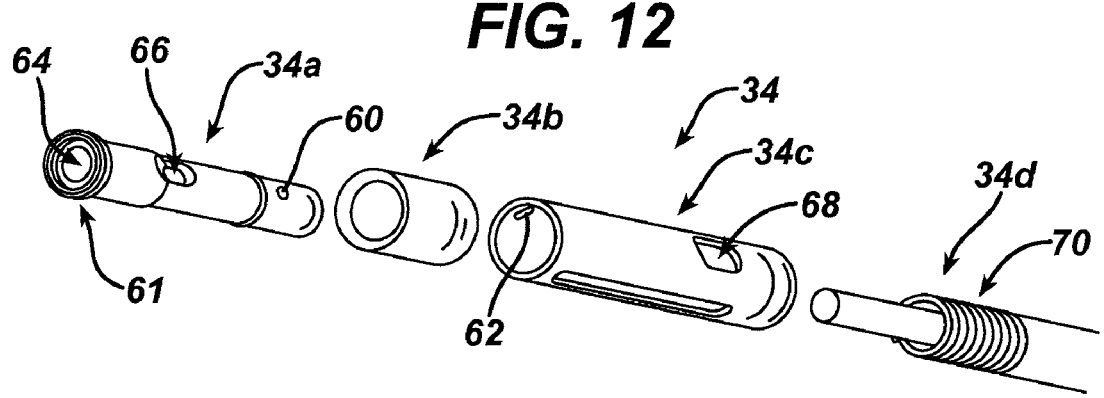
FIG. 12 is an exploded view of the knotting mechanism of FIG. 11.

In the illustrated exemplary embodiment, the knotting mechanism 34 is disposed around the shaft 28 and within the sheath 38 and includes an inner portion 34a, an outer portion 34b, a slotted outer portion 34c, and a cutting mechanism 34d. The knotting element 34 can have any size, shape, and configuration, but in an exemplary embodiment the knotting element 34 is substantially hollow and cylindrical and is sized to slidably move within the sheath 38. Generally, the inner portion 34a, an outer portion 34b, a slotted outer portion 34c, and a cutting mechanism 34d can be held in a coaxial relationship along the shaft 28. The inner portion 34a can be at least partially disposed inside and releasably coupled to the slotted outer portion 34c using a coupling mechanism such as interlocking protrusions 60 formed on the inner portion 34a that can click or snap into corresponding holes 62 formed in the slotted outer portion 34c. The inner portion 34a can also be at least partially disposed within the outer portion 34b, which can be disposed distal to the slotted outer portion 34c such that a proximal end of the outer portion 34b engages a distal end of the slotted outer portion 34c. The first portion 34a can include a distal rim 61 configured to mate with a distal end of the outer portion 34b, e.g., using interlocking protrusions and holes and/or other engagement mechanism, as will be appreciated by a person skilled in the art. The first and second sutures 32a, 32b attached to the first and second suture anchors 10a, 10b can be disposed through an opening 64 in a distal end of the knotting element's inner portion 34a, extend through a partial length of the inner portion 34a, exit the inner portion 34a through a side opening 66 formed in a sidewall thereof, and reenter the knotting mechanism 34 through an opening 68 formed in a sidewall of the slotted outer portion 34c. The interlocking protrusions 60 and the corresponding holes 62 can be respectively positioned on the inner portion 34a and the slotted outer portion 34c to axially align the side opening 66 and the opening 68 on a same side of the device 26 when the inner portion 34a and the slotted outer portion 34c are connected together, as best seen in FIGS. 4 and 11, to help minimize suture twisting and minimize lengths of suture extending between the openings 66, 68. Optionally, at least a portion of the edges of one or both of the side opening 66 and the opening 68 can be coated with a protective material such as an epoxy resin or a plastic polymer to reduce any potential for the knotting mechanism 34 to sever a suture during operation of the knotting mechanism 34.

The slotted outer portion 34c can be configured to be advanced, e.g., from the handle portion 40, to advance the outer portion 34b over the inner portion 34a, with portions of the sutures 32a, 32b extending out the inner portion's opening 66 being caught within the outer portion 34b as the outer portion 34b is advanced and mated to the inner portion 34a, thereby knotting the sutures 32a, 32b between the inner and outer portions 34a, 34b. Alternatively or in addition, the inner portion 34a can be configured to be proximally pulled to move the inner portion 34a within the outer portion 34b to mate the inner and outer portions 34a, 34b. The inner portion 34a can include a frangible joint adjacent its side opening 66 that is configured to "break" after the outer portion 34 has been advanced over and mated with the portion of the inner portion 34a distal to the side opening 66 to knot the sutures 32a, 32b. The cutting mechanism 34d can be at least partially disposed proximal to the slotted outer portion 34c and be configured to be advanced to cut excess lengths of the sutures 32a, 32b proximal to the outer portion 34b disposed over the inner portion 34a, e.g., using a coil 70 at a distal end of the cutting mechanism 34d. The cutting mechanism 34d preferably has a longitudinal length sufficient to permit the inner and outer portions 34a, 34b to be deployed off the device 26. The cutting mechanism 34d can be advanced through manipulation of a control on the device's handle portion 40 such as a slider or a ratcheting trigger, or by any other control means as will be appreciated by a person skilled in the art. A person skilled in the art will appreciate that the knotting mechanism 34 can be used to "knot" the sutures 32a, 32b without tying the sutures 32a, 32b together but by otherwise securing the sutures 32a, 32b, such as by applying a securing element to the sutures 32a, 32b or, as in this illustrated embodiment, locking the sutures 32a, 32b in an interference or friction fit between the inner and outer portions 34a, 34b.

The first and second sutures 32a, 32b mated to the first and second suture anchors 10a, 10b can be coupled to the knotting mechanism 34 at any time. In an exemplary embodiment, the knotting mechanism 34 can be loaded onto the shaft 28 before the anchors 10a, 10b are loaded onto the shaft 28 and before their associated sutures 32a, 32b are coupled with the knotting mechanism 34. The anchors 10a, 10b can be loaded onto the shaft 28 and the sutures 32a, 32b can be routed to pass through at least partially through the inner portion 34a and to extend alongside the outer portion 34b and alongside at least partially alongside the slotted outer portion 34c. At least one of the shaft 28, the first and second pusher shafts 36a, 36b, the sheath 38, the outer portion 34b, and/or the slotted outer portion 34c can optionally include at least one suture slot formed in an external surface thereof and configured to seat at least one of the sutures 32a, 32b extending thereacross. The remainders of the sutures 32a, 32b can extend alongside the slotted outer portion 34c and the cutting mechanism 34d within the sheath 38 and/or within a working channel of a scoping device used to introduce the device 26 into a body and can exit the device 26 adjacent to the handle portion 40.

As indicated above, the surgical device 26 can also include the outer tube or sheath 38 through which the shaft 28, the knotting mechanism 34, and the anchors 10a, 10b can be disposed. The sheath 38 is optional, as will be appreciated by a person skilled in the art, although use of the sheath 38 can help protect components of the device 26 from damage, fluid, tissue debris, interference with other devices, etc. In an exemplary embodiment, the sheath 38 can be composed of at least one biocompatible and flexible material to allow the sheath 38 to be passable through a tortuous pathway and to be introduced into a body of a patient through a working channel of a flexible scoping device (or through an auxiliary channel of a flexible scoping device) having at least its distal end disposed in a body. The sheath 38 can have any size, shape, and configuration. In an exemplary embodiment, the sheath 38 can be substantially cylindrical. The sheath 38 can have a uniform or non-uniform diameter along its longitudinal length. In an exemplary embodiment, the sheath 38 can have a diameter of equal to or less than about 3.5 mm.

Figure 13:
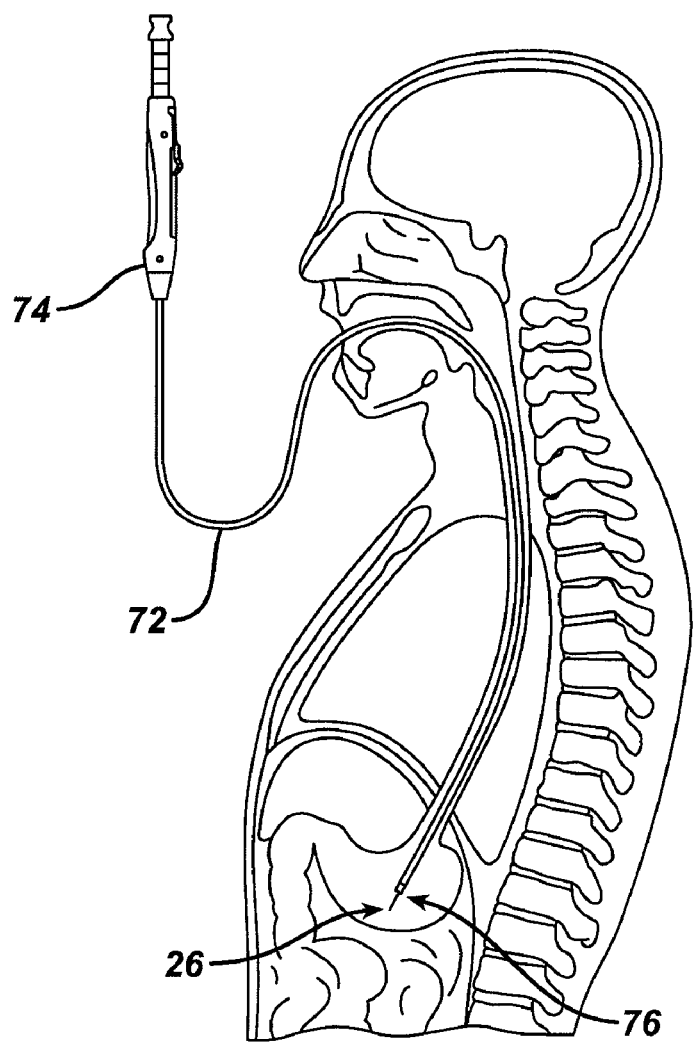
FIG. 13 is a schematic view of a flexible endoscope inserted into the upper gastrointestinal tract of a patient.

FIGS. 13-20 illustrate the device 26 in use in a minimally invasive surgical procedure to deliver and apply at least one of a plurality of anchors to a tissue of a patient. FIG. 13 illustrates a flexible endoscopic portion 72 of a scoping device, e.g., an endoscope 74, inserted into the upper gastrointestinal tract of a patient with the device 26 disposed therein with the device's distal end, e.g., a distal end of the sheath 38 and/or the shaft's tip 46, extending beyond a distal end 76 of the endoscope 74. The device 26 is preferably delivered to a surgical site beyond the endoscope's distal end 76 through a working channel 78 of the endoscope 74 in a manner known to a person skilled in the art, e.g., by manipulating a proximal end of the shaft 28 extending outside a proximal end of the endoscope 74 after the endoscope's distal end 76 has been advanced to a desired location adjacent tissue, although the device 26 can be delivered to a surgical site in other ways and at any time during a surgical procedure. Although FIGS. 13-20 illustrate the use of the device 26 in an endoscopic procedure involving a system that includes the endoscope 74 having a working channel 78 through which the device 26 can be delivered to a surgical site, a person skilled in the art will appreciate that these and/or similar devices can be used in other ways in other types of surgical procedures. Furthermore, the tissue to which the anchor is attached can be any tissue, e.g., the stomach wall, the intestinal wall, the colon, etc.

Figure 14:
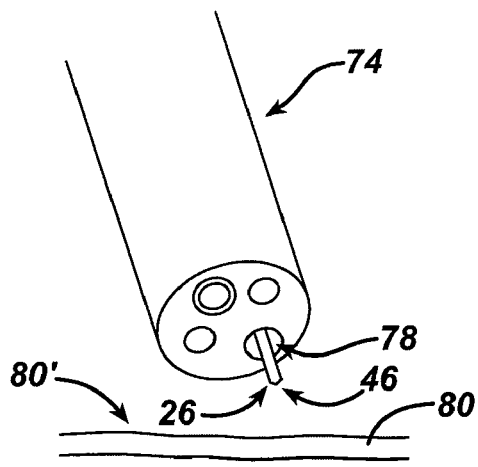
FIG. 14 is a side partially cross-sectional view of the device of FIG. 4 advanced through the endoscope of FIG. 13 and positioned adjacent to tissue.

As shown in FIG. 14, the tip 46 of the shaft 28 with the anchors 10a, 10b coupled to the shaft 28 can be positioned near a tissue 80. The tip 46 is in an extended position in FIG. 14 where it extend beyond distal ends of the anchors 10a, 10b, but the tip 46 is preferably in a retracted position and disposed between the anchors 10a, 10b when the device 26 is advanced through the working channel 78 of the endoscope 74. The tip 46 can be moved from the retracted position to the extended position at any time during the surgical procedure, such as when the device 26 has been advanced adjacent to the tissue 80. Any length of the device 26 can be advanced beyond the endoscope's distal end 76 in so positioning the tip 46. The tip 46 and the anchors 10a, 10b can be positioned at any angle with respect to a contact surface 80' of the tissue 80.

Figure 15:
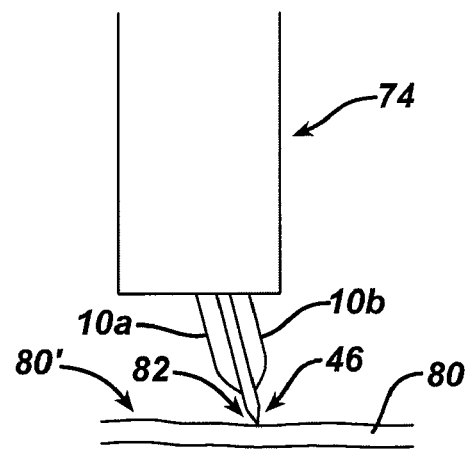
FIG. 15 is a side partially cross-sectional view of a tissue-penetrating tip in the device of FIG. 14 being moved to penetrate through the tissue.

FIG. 15 shows the device 26 in a penetration position, e.g., with the tip 46 in the extended position and in contact with the contact surface 80' of the tissue 80 where the tip 46 can begin to at least partially penetrate the tissue 80 at a first location 82. The tip 46 can be moved in any way, e.g., pushed, rotated, etc., to penetrate the tissue 80, as will be appreciated by a person skilled in the art. The tip's movement, in combination with the tapered shape of the tip 46 and/or the tapered shape of the distal ends 18a, 18b of the anchors 10a, 10b, can create or increase the size of an opening in the tissue 80. Alternatively or in addition, the opening in the tissue 80 can be maintained and/or increased by the use of other devices (not shown). Furthermore, the device 26 can optionally include an expandable member, e.g., a balloon, disposed around a portion of the sheath 38 that is configured to expand radially to increase a size of a tissue opening.

With the opening formed at the first location 80, the shaft 28 can be advanced through the tissue opening to effect a surgical procedure. Optionally, after the shaft 28 has been inserted at least partially through the tissue 80, the tip 46 can be proximally moved into its retracted position where it disposed between the anchors 10a, 10b.

Figure 16:
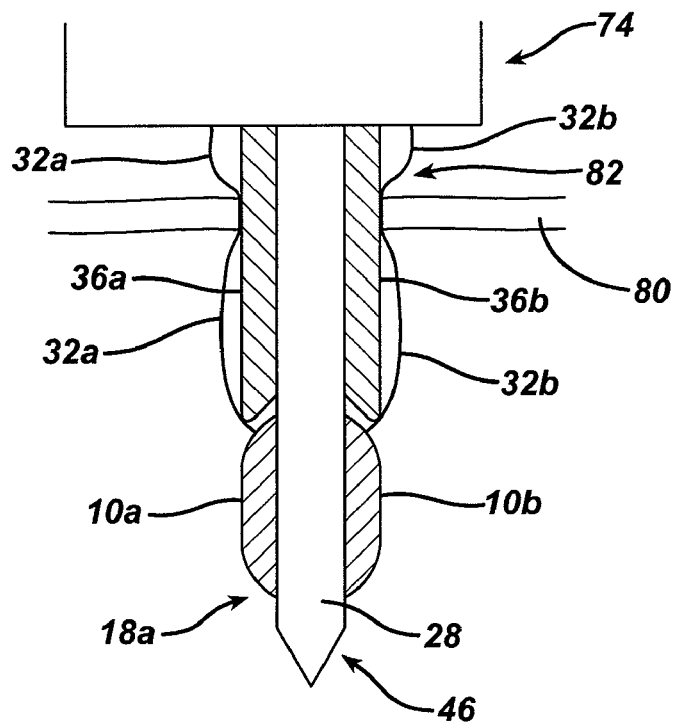
FIG. 16 is a side partially cross-sectional view of the device advanced through the tissue of FIG. 15.

FIG. 16 shows the device 26 in an advanced position with at least a portion thereof inserted through the opening in the tissue 80 created by the tip 46 at the first location 82 and inside a body cavity distal to the penetrated tissue 80. The tip 46 of the shaft 28 is illustrated as extending beyond distal ends 18a, 18b of the anchors 10a, 10b, but the tip 46 can be retracted at any time following its penetration through the tissue 80. FIG. 16 also shows the device 26 positioned in a pre-anchor-deployment position where the anchors 10a, 10b and at least a portion of the pusher shafts 36a, 36b are positioned distal to the penetrated tissue 80. Such a pre-anchor-deployment position allows any of the anchors 10a, 10b to be deployed distal to the tissue 80 while allowing the suture(s) 32a, 32b attached to the deployed anchor(s) 10a, 10b to pass through the tissue 80. In the pre-anchor-deployment position, the knotting mechanism 34 (not shown in FIG. 16) can be positioned distal or proximal to the tissue 80, but at least a portion of the knotting mechanism 34 is preferably positioned distal to the tissue 80, e.g., advanced through the opening formed by the tip 46. The device 26 can optionally include a tissue stop, e.g., one or more protruding members located on an outside surface of the device 26, to help limit the penetration depth of the device 26 through the tissue 80 and to help prevent injury to tissue on the distal, "blind" side of the tissue 80 being penetrated. Various tissue stops can be used as will be appreciated by a person skilled in the art, with non-limiting examples of a tissue stop described in previously mentioned U.S. Patent Publication No. 2007/0112385.

Figure 17:
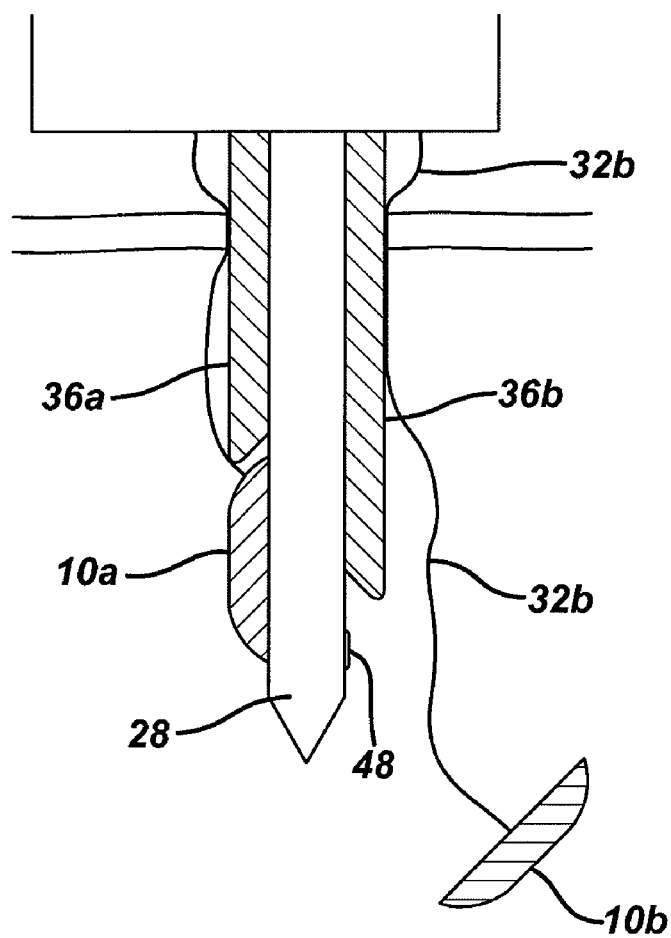
FIG. 17 is a side partially cross-sectional view of a first suture anchor deployed from the device of FIG. 16.

Once the anchors 10a, 10b are positioned as desired with respect to the tissue 80, one or more anchors 10a, 10b can be deployed from the shaft 28. Deployment can be achieved by advancing a selected one of the pusher shafts 38a, 38b relative to its associated one of the anchors 10a, 10b, thereby pushing the associated anchor and releasing it from the shaft 28. As mentioned above, the anchors 10a, 10b can be simultaneously or sequentially deployed. In the illustrated exemplary embodiment, FIG. 17 shows one of the anchors, e.g., the second anchor 10b, deployed into the body cavity distal to the penetrated tissue 80 following actuation of the anchor actuator, e.g., the second pusher shaft 36, with the first anchor 10a still removably coupled to the shaft 28. The protrusion 48 that engages the second anchor 10b can help deploy the second anchor 10b from the shaft 28 and rotate the second anchor 10b, as shown. The second anchor's attached suture 32b extends from the second anchor 10b, through the tissue 80, and into the knotting element 34 (not shown).

Figure 18:
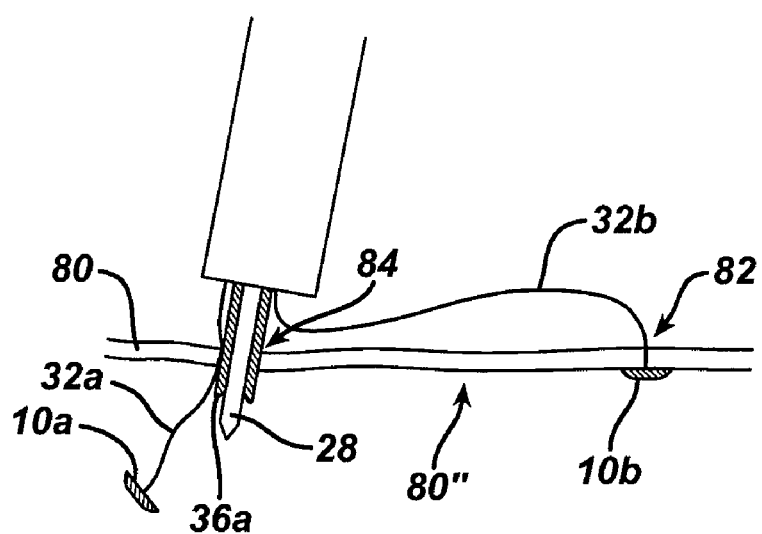
FIG. 18 is a side partially cross-sectional view of a second suture anchor deployed from the device of FIG. 17.

FIG. 18 shows the deployed second anchor 10b being drawn against a distal side 80" of the tissue 80 substantially at the first location 82 by, e.g., a tensile force being applied to its associated suture 32b. Since the second suture 32b is attached to a mid-portion of the elongate body of the second anchor 10b, the tensile force can cause the second anchor 10b to pivot approximately 90 degrees to lie substantially parallel to the distal tissue surface 80", thereby engaging the tissue 80. FIG. 18 also shows the second anchor 10 deployed and rotated, e.g., with the anchor's longitudinal axis no longer substantially axially aligned with the shaft's longitudinal axis, which it was pre-deployment. FIG. 18 further shows the shaft 28 withdrawn from the first location 82 and advanced through the tissue 80 at a second location 84. The shaft 28 can be positioned adjacent the second location 84 and the tip 46 can form an opening in the tissue 80 at the second location 84 similar to that described above for the first location 82. Also similar to that described for the second anchor 10b at the first location 82, another one of the plurality of anchors coupled to the shaft 28, e.g., the first anchor 10a, can be deployed from the shaft 28 as shown in FIG. 18 by advancing the first pusher shaft 36a associated with the first anchor 10a. Deployment of the first and second anchors 10a, 10b can thus be achieved without removing the device 26 from the patient's body.

Figure 19:
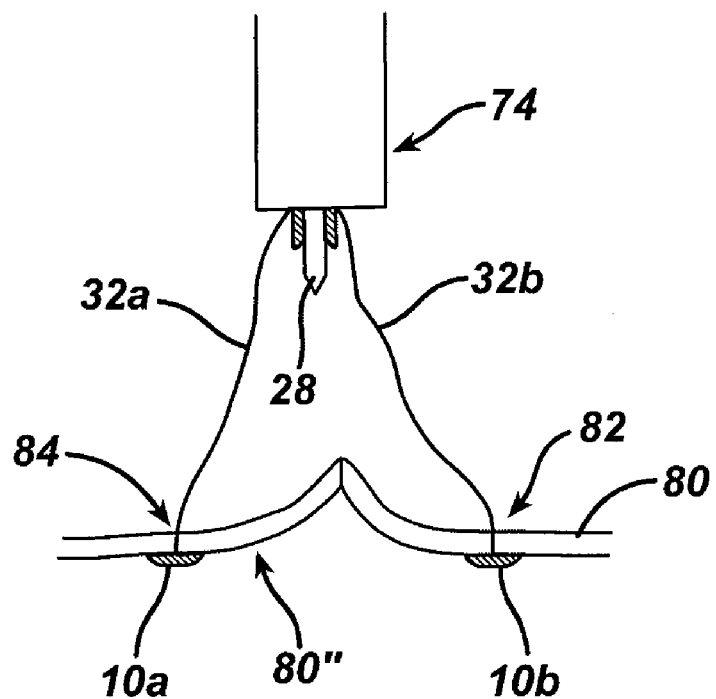
FIG. 19 is a side partially cross-sectional view of the deployed first and second suture anchors with sutures attached thereto and of the device removed from the tissue of FIG. 18.
Figure 20:
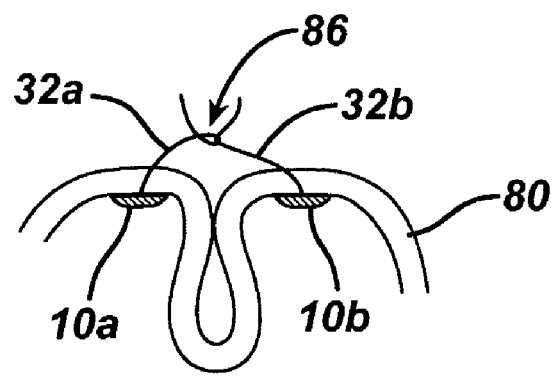
FIG. 20 is a side partially cross-sectional view of secured sutures attached to the deployed first and second suture anchors of FIG. 19.

FIG. 19 shows the first and second deployed anchors 10a, 10b being drawn against the distal tissue surface 80" of the tissue 80 substantially at the first and second locations 82, 84, respectively. The first and second anchors 10a, 10b can be so moved by, e.g., applying a tensile force to their respective attached sutures 32a, 32b, thereby manipulating the anchors 10a, 10b and at least a portion of the tissue 80. FIG. 19 also shows the device 26 being withdrawn from the tissue 80 and moving into the working channel 78. The sutures 32a, 32b attached to the deployed anchors 10a, 10b can extend through the tissue 80 substantially at the first and second locations 82, 84, respectively, and into the knotting mechanism 34 (not shown). The sutures 42a, 42b extending through the first and second locations 82, 84 can be secured together to help appose the tissue 80 using the knotting mechanism 34 to help secure the first and second anchors 10a, 80b.

As discussed above and as shown in FIG. 20, a knotting element 86, e.g., the inner and outer portions 34a, 34b of the knotting element 34, can be disposed at the proximal ends of the sutures 32a, 32b associated with the deployed anchors 10a, 10b. In an exemplary embodiment, when the tissues have been properly apposed, the knotting element 34 can be "fired" by manipulating the slotted outer portion 34c and to apply force to the outer portion 34b, which is disposed around the inner portion 34a. If sufficient force is applied, the protrusions 60 formed on the inner portion 34a can distort and become released from engagement with the holes 62 formed in the slotted outer portion 34c, permitting the outer portion 34b to distally slide until it abuts the inner portion 34a, e.g., at the inner portion's distal rim 61. Alternatively, the inner portion 34a can be proximally pulled to release the inner portions 34a from the slotted outer portions 34c until the inner portion's distal rim 61 engages the outer portion 34b, thereby providing a movement "stop" for the inner portion 34a and knotting the sutures 32a, 32b. Application of sufficient force can also break the inner portion's frangible joint and separate the inner portion 34a. The mating of the inner and outer portions 34a, 34b will "knot" the sutures 32a, 32b as discussed above. The tissue 80 can thereby be drawn together substantially at the first and second locations 82, 84 to appose tissue between the first and second locations 82, 84. Any excess suture extending from the anchors 10a, 10b can be trimmed near the knotting element 86, if desired, by advancing the cutting mechanism 34d to engage and cut the sutures 32a, 32b or in any other way, e.g., using an endoscopic cutting instrument, as will be appreciated by a person skilled in the art.

One or both of the device 26 and the endoscope 74 can be removed from the surgical site and the patient's body at any point following sufficient securing of the tissue 80 and/or other tissue using any number of the plurality of anchors coupled to the shaft 28. Following the device's removal from the body, e.g., by retracting the device 26 through the endoscope's working channel 78, the device 26 can optionally be reloaded with one or more suture anchors to be deployed, e.g., by sliding the anchors onto the shaft's flanges 54. Another knotting element can also be reloaded into the device 26 and sutures attached to the anchors can be threaded through the reloaded knotting element. The device 26, along with any reloaded elements, can be advanced again into the body through the endoscope 74 or in any other way, and the reloaded anchor(s) can be deployed and secured as discussed above. Such removal, reloading, and reintroduction of the device 26 can repeat as many times as desired during a surgical procedure.

A person skilled in the art will appreciate that the present invention has application in conventional endoscopic and open surgical instrumentation as well application in robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical device, comprising:
    an elongate shaft having a sharp distal tip;
    a plurality of suture anchors releasably coupled to the shaft and configured to have the tip selectively disposed therebetween, each of the plurality of suture anchors having a length of suture extending therefrom;
    at least one anchor actuator, each anchor actuator configured to selectively and independently deploy the plurality of suture anchors; and
    a knotting mechanism disposed around the shaft and configured to apply a knotting element to the lengths of suture extending from each of the plurality of suture anchors after the plurality of anchors have been deployed.

2. The device of claim 1, wherein the tip is substantially planar.

3. The device of claim 1, wherein at least one of the tip and at least one of the plurality of suture anchors is movable to selectively position the tip distally to distal ends of the plurality of suture anchors.

4. The device of claim 1, wherein the anchor actuator includes first and second elongate pusher shafts, the first pusher shaft being configured to deploy a first one of the plurality of suture anchors and the second pusher shaft being configured to deploy a second one of the plurality of suture anchors.

5. The device of claim 4, wherein a distal end of the first pusher shaft is configured to engage a proximal end of the first one of the plurality of suture anchors and a distal end of the second pusher shaft is configured to engage a proximal end of the second one of the plurality of suture anchors.

6. The device of claim 1, further comprising a sheath disposed around the shaft.

7. The device of claim 1, further comprising a handle portion engaged with the at least one anchor actuator and configured to be manipulatable outside a body.

8. The device of claim 1, wherein the plurality of suture anchors each have a tapered distal tip.

9. The device of claim 1, wherein the shaft is flexible such that the shaft can be passed through a tortuous pathway.

10. A surgical device, comprising:
    an elongate shaft having a tip at a sharp distal end thereof;
    at least two suture anchors removably coupled to an outside surface of the shaft configured to have the tip selectively disposed therebetween, each suture anchor having a suture mated thereto;
    a knotting mechanism disposed around the shaft and configured to selectively apply a knotting element to the sutures mated to the at least two suture anchors; and an elongate sheath, wherein the shaft is movably disposed in the sheath such that the tip can selectively extend beyond a distal end of the sheath, and wherein the sheath is configured to have the knotting mechanism and the at least two suture anchors movably disposed therein.

11. The device of claim 10, further comprising an anchor actuator configured to selectively and independently deploy the at least two suture anchors.

12. The device of claim 10, wherein longitudinal axes of each of the at least two suture anchors are substantially parallel to a longitudinal axis of the shaft at least when the at least two suture anchors are coupled to the outside surface of the shaft.

13. The device of claim 10, wherein the shaft is configured to be disposed in a body through a working channel of a scoping device.

14. A surgical device, comprising:
an elongate shaft having a sharp distal tip;
a plurality of suture anchors releasably coupled to the shaft and configured to have the tip selectively disposed therebetween, each of the plurality of suture anchors having a length of suture extending therefrom; and
at least one anchor actuator, each anchor actuator configured to selectively and independently deploy the plurality of suture anchors;
wherein the shaft has at least one protrusion laterally extending therefrom adjacent to the tip that is configured to rotate at least one of the plurality of suture anchors when the at least one of the plurality of suture anchors is deployed.

* * * * *